United States Patent
Mitariten

(10) Patent No.: US 7,442,233 B2
(45) Date of Patent: Oct. 28, 2008

(54) INTEGRATED HEAVY HYDROCARBON REMOVAL, AMINE TREATING AND DEHYDRATION

(75) Inventor: Michael J. Mitariten, Pittstown, NJ (US)

(73) Assignee: BASF Catalysts LLC, Florham Park, NJ (US)

( * ) Notice: Subject to any disclaimer, the term of this patent is extended or adjusted under 35 U.S.C. 154(b) by 419 days.

(21) Appl. No.: 11/175,460

(22) Filed: Jul. 6, 2005

(65) Prior Publication Data

US 2007/0006729 A1    Jan. 11, 2007

(51) Int. Cl.
B01D 53/26 (2006.01)
C07C 7/11 (2006.01)
C07C 7/12 (2006.01)

(52) U.S. Cl. .............................. 95/123; 95/143; 95/235; 96/4; 96/122; 96/130; 96/134; 423/228; 585/820

(58) Field of Classification Search .................. 96/4, 96/121, 122, 130, 134, 146, 234, 355; 95/43, 95/49, 51, 117, 121–123, 143, 148, 149, 95/235, 236; 423/220, 228, 229; 585/820, 585/833

See application file for complete search history.

(56) References Cited

U.S. PATENT DOCUMENTS

| | | | | |
|---|---|---|---|---|
| 3,728,844 A * | 4/1973 | Snyder et al. | 95/125 |
| 3,751,878 A | 8/1973 | Collins | 55/58 |
| 3,841,058 A | 10/1974 | Templeman | 55/33 |
| 4,061,724 A | 12/1977 | Grose et al. | 423/335 |
| 4,070,165 A | 1/1978 | Colton | 55/30 |
| 4,073,865 A | 2/1978 | Flanigen et al. | 423/339 |
| 4,077,779 A | 3/1978 | Sircar et al. | 55/25 |
| 4,130,403 A | 12/1978 | Cooley et al. | 55/16 |
| 4,150,962 A | 4/1979 | Colton | 62/17 |
| 4,152,217 A | 5/1979 | Eisenberg et al. | 203/2 |
| 4,310,440 A | 1/1982 | Wilson et al. | 252/435 |
| 4,421,535 A | 12/1983 | Mehra | 62/17 |
| 4,440,871 A | 4/1984 | Lok et al. | 502/214 |
| 4,484,933 A | 11/1984 | Cohen | 55/25 |
| 4,511,381 A | 4/1985 | Mehra | 62/17 |
| 4,567,027 A | 1/1986 | Detournay et al. | 423/101 |
| 4,639,257 A | 1/1987 | Duckett et al. | 55/16 |
| 4,702,898 A | 10/1987 | Grover | 423/220 |
| 4,770,676 A | 9/1988 | Sircar et al. | 55/26 |
| 4,775,397 A | 10/1988 | Porembski | 55/97 |
| 4,853,202 A | 8/1989 | Kuznicki | 423/326 |
| 4,857,083 A | 8/1989 | DiMartino | 55/26 |

(Continued)

OTHER PUBLICATIONS

"Operations and Recovery Improvement Via Heavy Hydrocarbon Extraction", Iyengar, et al., Presented at Laurance Reid Gas Conditioning Conference, Norman, Oklahoma—Mar. 1-4, 1998 pp. 161-174.

*Primary Examiner*—Frank M. Lawrence
(74) *Attorney, Agent, or Firm*—Raymond F. Keller

(57) ABSTRACT

The present invention is directed to an improved integrated process for the removal of heavy hydrocarbons, carbon dioxide, hydrogen sulfide, and water from a raw natural gas feed stream. More specifically, the integrated process of the present invention comprises a three step process involving the adsorption of heavy hydrocarbons and water on an adsorbent bed selective for the same, a subsequent aqueous lean amine treatment for the absorptive removal of acid gases, such as carbon dioxide and hydrogen sulfide, and an adsorptive removal of water. The process of the present invention results in a highly purified natural gas product stream.

20 Claims, 3 Drawing Sheets

U.S. PATENT DOCUMENTS

| | | | |
|---|---|---|---|
| 4,935,580 A | 6/1990 | Chao et al. | 585/820 |
| 4,938,989 A | 7/1990 | Steeves et al. | 426/658 |
| 4,957,715 A * | 9/1990 | Grover et al. | 423/228 |
| 4,978,439 A | 12/1990 | Carnell et al. | 208/91 |
| 5,012,037 A | 4/1991 | Doshi et al. | 585/822 |
| 5,089,034 A | 2/1992 | Markovs et al. | 55/28 |
| 5,233,837 A | 8/1993 | Callahan | 62/38 |
| 5,244,650 A | 9/1993 | Kuznicki et al. | 423/718 |
| 5,248,488 A * | 9/1993 | Yan | 423/210 |
| 5,288,034 A | 2/1994 | Schönmeier et al. | 242/58.3 |
| 5,486,227 A | 1/1996 | Kumar et al. | 95/41 |
| 5,664,411 A | 9/1997 | Shao | 60/39.02 |
| 5,726,118 A | 3/1998 | Ivey et al. | 502/417 |
| 5,746,788 A | 5/1998 | Schmidt et al. | 48/198.2 |
| 5,766,311 A | 6/1998 | Ackley et al. | 95/115 |
| 5,840,099 A | 11/1998 | Kratz et al. | 95/101 |
| 5,846,295 A | 12/1998 | Kalbassi et al. | 95/105 |
| 5,994,147 A | 11/1999 | Rodriguez et al. | 436/163 |
| 6,105,365 A | 8/2000 | Deeba et al. | 60/274 |
| 6,183,539 B1 | 2/2001 | Rode et al. | 95/117 |
| 6,251,165 B1 * | 6/2001 | Jullian et al. | 95/115 |
| 6,444,012 B1 | 9/2002 | Dolan et al. | 95/99 |
| 6,497,750 B2 | 12/2002 | Butwell et al. | 95/96 |
| 6,506,349 B1 | 1/2003 | Khanmamedov | 423/210 |
| 6,521,020 B2 * | 2/2003 | Butwell et al. | 95/99 |
| 6,599,347 B2 | 7/2003 | Kalbassi et al. | 95/10 |
| 6,610,124 B1 | 8/2003 | Dolan et al. | 95/98 |
| 6,797,854 B1 | 9/2004 | Jochem | 585/822 |
| 6,918,948 B2 | 7/2005 | Jaussaud et al. | 95/116 |
| 7,211,128 B2 * | 5/2007 | Thomas et al. | 95/135 |
| 2001/0049998 A1 | 12/2001 | Rode et al. | 95/117 |
| 2002/0134234 A1 | 9/2002 | Kalbassi et al. | 95/11 |
| 2007/0006732 A1 * | 1/2007 | Mitariten | 95/237 |

* cited by examiner

INTEGRATED HEAVY HYDROCARBON REMOVAL, AMINE TREATING AND DEHYDRATION

FIELD OF THE INVENTION

The present invention relates generally to a method for the improved purification of natural gas feed streams. More specifically, the present invention relates to a process for the removal of heavy hydrocarbons, water, and acid gases and the recovery of heavy hydrocarbons, from natural gas by use of a novel integrated process.

BACKGROUND OF THE INVENTION

The removal of the acid gas components carbon dioxide and hydrogen sulfide from natural gas is of considerable importance inasmuch as these components can be present to a significant extent. Carbon dioxide and hydrogen sulfide contamination lower the heating value of the natural gas and cause corrosion concerns and increase the transportation cost based on unit heating value. For these reasons carbon dioxide commonly requires removal to a level of 2% or less and hydrogen sulfide must often be removed to levels of 4 ppm or less for pipeline transportation of natural gas. These components also have a high freezing point and for this reason must be almost completely removed from natural gas prior to processing in liquefied natural gas (LNG) plants.

Methods heretofore known for purification of natural gas, in particular, acid gas removal may be divided roughly into three classifications:

(a) Methods involving amine adsorption treatment where the amine forms weak bonds with the acid gases at relatively low processing temperatures and (usually) high pressure. The rich amine solvent is regenerated by decreasing its pressure and increasing its temperature in an amine stripper. The acid gas components are then removed.

(b) By adsorption using a physical solvent at relatively low temperatures and relatively high pressures wherein the solubility of the acid gas components is greater than that of light hydrocarbons. The physical solvent is generally regenerated by pressure reduction causing the dissolved gases to flash from the solvent.

(c) Miscellaneous processes involving selective diffusion of the gases through a series of polymeric membranes, wherein the acid gas-contaminated natural gas feed is introduced at high pressure and the acid gas components due to higher solubility and diffusion principles permeate across the membrane from high pressure to low pressure held on the permeate side of the membrane.

A principal disadvantage of the amine treatment adsorption is that water will be reintroduced into the natural gas stream by the aqueous amine solvent. Further, the use of solvents, in particular, volatile organic solvents is being discouraged if not out right banned by government agencies in order to reduce both water and air pollutions.

For smaller volume applications, especially where gas flows are less than five to ten million cubic feet per day, considerable attention has been given to the development of pressure swing adsorption (PSA) processes for removal of gaseous impurities such as $CO_2$.

Numerous patents describe PSA processes for separating carbon dioxide from methane or other gases. One of the earlier patents in this area is U.S. Pat. No. 3,751,878, which describes a PSA system using a zeolite molecular sieve that selectively adsorbs $CO_2$ from a low quality natural gas stream operating at a pressure of 1000 psia, and a temperature of 300° F. The system uses carbon dioxide as a purge to remove some adsorbed methane from the zeolite and to purge methane from the void space in the column. U.S. Pat. No. 4,077,779, describes the use of a carbon molecular sieve that adsorbs $CO_2$ selectively over hydrogen or methane. After the adsorption step, a high pressure purge with $CO_2$ is followed by pressure reduction and desorption of $CO_2$ followed by a rinse at an intermediate pressure with an extraneous gas such as air. The column is then subjected to vacuum to remove the extraneous gas and any remaining $CO_2$.

U.S. Pat. No. 4,770,676, describes a process combining a temperature swing adsorption (TSA) process with a PSA process for the recovery of methane from landfill gas. The TSA process removes water and minor impurities from the gas, which then goes to the PSA system, which is similar to that described in U.S. Pat. No. 4,077,779 above, except the external rinse step has been eliminated. $CO_2$ from the PSA section is heated and used to regenerate the TSA section. U.S. Pat. No. 4,857,083, claims an improvement over U.S. Pat. No. 4,077,779 by eliminating the external rinse step and using an internal rinse of secondary product gas ($CO_2$) during blowdown, and adding a vacuum for regeneration. The preferred type of adsorbent is activated carbon, but can be a zeolite such as 5A, molecular sieve carbons, silica gel, activated alumina or other adsorbents selective for carbon dioxide and gaseous hydrocarbons other than methane.

As above noted, it is well-known to remove acid gases such as hydrogen sulfide and carbon dioxide from natural gas streams using an amine system wherein the acid gases are scrubbed from the feed with an aqueous amine solvent with the solvent subsequently stripped of the carbon dioxide or other acid gases with steam. These systems are widely used in industry with over 600 large units positioned in natural gas service in the U.S. The amine solvent suppliers compete vigorously and the amines used range from diethanol amine (DEA) to specialty formulations allowing smaller equipment and operating costs while incurring a higher solvent cost. These systems are well accepted although they are not very easy to operate. Keeping the amine solvents clean can be an issue.

Again, a disadvantage to using aqueous amines is that the natural gas product of an aqueous amine system is water saturated. Accordingly, dehydration typically using glycol absorption would be required on the product stream after the carbon dioxide has been removed adding operational and capital costs to the purification process.

A further concern with amine treating of natural gas containing heavy hydrocarbons is that the heavy hydrocarbons can cause foaming of the amine solvent. Foaming of the solvent is undesired as it reduces the capacity of the system and can result in carryover of the solvent into the product gas stream.

The majority of the market supply of $C_2$ and $C_{3+}$ hydrocarbons are extracted from natural gas. For this reason these components are commonly termed natural gas liquids (NGLs). The removal of the $C_{3+}$ hydrocarbons from natural gas is accomplished in three alternative routes.

In the first and oldest method, heavy oil is contacted with natural gas such that the lean oil wash adsorbs $C_{3+}$ components into the liquid. These components are then stripped from the oil and eventually recovered as a separate product. More recent designs use refrigerated oil but overall this technology is considered outdated. A second method of recovery of $C_{3+}$ hydrocarbons is through a refrigeration system where the natural gas feed is chilled to temperatures typically in the range of −30° F. and the $C_{3+}$ components are substantially condensed from the natural gas stream. A more efficient, though more expensive, method and means to recover ethane as well, is generally applied to large gas flows where a turbo-expander plant expands the natural gas to a lower pressure. This expansion causes a substantial drop in the temperature of the natural gas stream. Once more, $C_{3+}$ hydrocarbons are removed. As a general rule turbo-expander plants are favored where ethane recovery is desired or higher levels of $C_{3+}$ liquids recovery is justified. These plants are expensive, especially for recompression. All of the routes for liquid recovery are fairly expensive in capital and require considerable power for either refrigeration or recompression.

Hydrocarbons are also commonly removed from natural gas to prevent the condensation of liquids in pipeline transmission systems and pipelines commonly impose a dew point specification to prevent the condensation of the liquids. In meeting this specification, "dew point" plants, are commonly applied. Dew point plants target recovery of hydrocarbons, mainly heavier hydrocarbons. As with NGL recovery, quick cycle units, refrigeration or Joule-Thompson expansion plants can also be applied.

An alternate means to remove the heavy hydrocarbons from natural gas is to use a silica gel adsorbent in so called "quick cycle units" wherein the adsorbent has an affinity for heavy hydrocarbons, typically $C_6$ and heavier components. In such a means, the natural gas containing heavy hydrocarbons is passed through the bed of silica gel to trap $C_{6+}$ hydrocarbons. Regeneration is typically done by passing a pressurized and/or heated stream of natural gas feed or product gas through the adsorbent bed. After cooling the heavy hydrocarbons, contained in the effluent from the regeneration process, can be condensed as a liquid product and removed.

The relationship in value of natural gas to natural gas liquids is complex and the prices, while related, do fluctuate. Almost always, the components are more valuable as a liquid than as a gas and a typical increase in value is about 1.5× the value in the pipeline. The extraction of liquids is the main business of mid-stream processors.

The present assignee has developed processes for the recovery of hydrocarbons from natural gas utilizing pressure swing adsorption with Molecular Gate® sieves. These processes are described in U.S. Pat. No. 6,444,012, issued Sep. 3, 2002, and U.S. Pat. No. 6,497,750, issued Dec. 24, 2002. In the former application, the PSA process involves initially adsorbing $C_{3+}$ hydrocarbons from a natural gas stream in a first PSA unit containing a hydrocarbon-selective adsorbent to produce a first product stream comprising methane, nitrogen and reduced level of hydrocarbons relative to the feed. The first product stream is then directed to a second PSA adsorption unit containing a nitrogen selective adsorbent (Molecular Gate®) so as to adsorb nitrogen and produce a second product stream enriched with methane. Recovery of the hydrocarbons can be achieved by desorbing the first adsorbent with the methane product stream. In this way, the heat value of the $C_{3+}$ hydrocarbons is recaptured in the methane stream. The latter application is directed to a process of separating nitrogen from a feed natural gas stream in a first PSA unit containing a Molecular Gate® nitrogen-selective adsorbent to form a methane product stream, directing the tail gas from the first PSA unit to a second PSA unit containing a methane selective adsorbent so as to recover methane from the tail gas to form a nitrogen rich product stream and a tail gas stream comprising hydrocarbons and refrigerating the hydrocarbon-containing tail gas so as to knock out the $C_{3+}$ hydrocarbon liquids. The methane is then recycled to feed.

Typical pipeline specifications for $H_2S$ are 4 ppm and 2% for $CO_2$. Liquid natural gas (LNG) facilities generally require the near complete removal of these acid gases since the acid gases freeze at the temperatures of LNG. U.S. Pat. No. 4,702,898, issued to Grover discloses a process for the removal of acid gases from mixtures which utilizes an alkaline scrubbing solution to remove the acid gases, e.g., carbon dioxide, from the gas mixtures. In addition to acid gas adsorption, solid adsorbents, e.g., molecular sieves, can be employed for the further removal of carbon dioxide depending upon the ability of the liquid adsorption system to remove carbon dioxide and upper limits on the permissible carbon dioxide concentration. For example, adsorption is often employed when it is necessary to substantially remove carbon dioxide to levels of about 50 to 200 ppmv carbon dioxide, such as is typically required in liquefaction or deep ethane recovery. In some instances, it can be desirable to eliminate the liquid carbon dioxide adsorption unit and perform the carbon dioxide removal by molecular sieve adsorption alone, e.g., for purification where bulk carbon dioxide removal is not required (i.e., natural gas feeds low in acid gas components).

As discussed above, a particular disadvantage of the amine solvent treatment for removal of acid gases is that the solvents are used as a mixture with liquid water, and thus, the natural gas product from the amine treatment plant is saturated in water vapor. This requires downstream dehydration, which mostly commonly uses glycol solvents. For LNG plants extremely low water dew points are required and molecular sieve (or other adsorbents) are commonly applied, sometimes downstream of a glycol unit where the glycol serves for bulk water removal.

U.S. Pat. No. 3,841,058, issued to Templeman, discloses a method of purifying natural gas or the like to render it suitable for liquefaction. The method consists essentially of adsorbing water and methanol from a stream of natural gas containing water, methanol and carbon dioxide in a first bed of an adsorbent material and subsequently adsorbing the carbon dioxide in a second bed of adsorbent material. The first adsorber bed is regenerated by passing a gas therethrough at an elevated temperature, i.e., thermal swing adsorption. The second adsorber bed is regenerated by reducing the pressure within the bed and also by passing a gas therethrough at a low temperature to displace desorbed carbon dioxide from the adsorber bed, i.e., a pressure swing adsorption cycle. The patent discloses that the adsorption effluent gas from the first adsorber bed can be cooled to subambient temperatures to increase the adsorptive capacity of the molecular sieves for carbon dioxide.

The method disclosed in above-identified U.S. Pat. No. 3,841,058, however, does not provide an adequate solution to the problem of removing water and carbon dioxide prior to low temperature LNG processing. More specifically, because the second adsorber bed is regenerated by pressure swing adsorption, there is inherently less hydrocarbon recovery due to the fact that pressure swing cycles are usually operated at a shorter cycle time than thermal swing cycles, e.g., minutes versus hours, and hence, the hydrocarbon feed gas which remains in the void space after the adsorption step is terminated is lost in the desorption effluent stream when the adsorber bed is depressurized. In addition, because thermal swing adsorption cycles typically provide more complete regeneration than is generally possible with pressure swing cycles, higher residual carbon dioxide levels are present on the adsorbent subjected to pressure swing regeneration. The higher residual levels cause higher levels of carbon dioxide in the product gas since the concentration of carbon dioxide in the product gas is in equilibrium with the carbon dioxide adsorbed on the adsorbent in the effluent end of the adsorber bed. In order to keep the carbon dioxide content of the adsorbent low in the effluent end of the adsorber bed it is necessary to reduce the cycle time, however, reduced cycle times contribute to the recovery losses described above. Hence, the above-identified patent describes a process that is deficient due to the use of the pressure swing adsorption cycle in the second adsorber bed as compared to a thermal swing cycle.

Adsorption units using silica gels are used in a wide variety of applications. In the natural gas industry, one example application for silica gels is in adsorption drying. The use typically employs two or more adsorber vessels filled with adsorbent to remove water from natural gas, and produce a dry natural gas product. When the silica gel adsorbent is saturated with water, it is commonly regenerated using a portion of the feed gas or dry product gas, heated to high temperature (typically 300° to 500° F.) to strip the previously adsorbed water off the adsorber bed. Various flow schemes for recycling this regenerated stream, now containing water, exist in the industry.

However, a more common process for dehydration in the natural gas industry is the glycol dehydration process, in which a stream of glycol, for example triethylene glycol, is contacted against the incoming natural gas stream. The glycol solvent extracts water from the stream and a reduced water product is produced. The rich glycol stream is subsequently regenerated by pressure reduction and heating, after which it is pumped back as a lean stream to continue its water removal service.

Another common application for silica gel adsorbents is in quick cycle heavy hydrocarbon removal units. In this application, heavy hydrocarbons are adsorbed from natural gas product meeting hydrocarbon dew point requirements. As with water removal, the silica gel adsorbent, now saturated with heavy hydrocarbons, is regenerated at high temperatures, typically 500° F., using a portion of the feed stream or the hydrocarbon reduced product stream.

Another example of an application for silica gel in natural gas processing is its use to remove water vapor and heavy hydrocarbons upstream of a membrane unit used to remove $CO_2$. Such $CO_2$ removal membrane units operate by selective permeation of $CO_2$ from high pressure to low pressure across a polymeric membrane. Such membranes will lose treating capacity over time due to exposure to heavy hydrocarbons and silica gel adsorption processes are commonly used for the removal of both water and heavy hydrocarbons. Such membrane units are generally used only as bulk $CO_2$ removal devices and will commonly be followed by amine processing for final $CO_2$ removal. In this configuration, the first stage treatment will be a silica gel dew point unit to remove heavy hydrocarbons and water, followed by a membrane unit for bulk $CO_2$ removal, followed by an amine system for acid gas removal. The amine unit in this application re-introduces water vapor back into the product natural gas and, thus, downstream dehydration is subsequently required.

It is an object of the present invention to provide a novel and economically beneficial natural gas purification system for the adsorptive removal and recovery of heavy hydrocarbons ($C_{4+}$ hydrocarbons, or more preferably $C_{6+}$ hydrocarbons), water, and acid gases. The application of the integrated process of the present invention results in an improved process for the removal of heavy hydrocarbons, carbon dioxide, hydrogen sulfide, and water from raw natural gas.

SUMMARY OF THE INVENTION

In one aspect of the present invention, there is provided a multi-step adsorption/absorption process for separating heavy hydrocarbons, acid gases, and water from a raw natural gas feed stream. The process includes the steps of: (a) passing the raw natural gas feed through a first adsorption step containing a heavy hydrocarbon and water selective adsorbent bed and withdrawing a first adsorption effluent stream comprising dehydrated natural gas and having a reduced amount of heavy hydrocarbons relative to the natural gas feed stream; (b) passing the first adsorption effluent stream through an absorption step comprising an aqueous lean amine treatment for the removal of acid gases such as carbon dioxide and hydrogen sulfide and withdrawing an absorption effluent stream comprising a natural gas stream substantially free of carbon dioxides and hydrogen sulfides relative to the first adsorption effluent stream; and (c) subjecting the absorption effluent stream to a second adsorption step containing a heavy hydrocarbon and water selective adsorbent bed for the dehydration of the product natural gas relative to the absorption effluent stream.

In another aspect of the presenting invention, the multi-step adsorption/absorption process comprises an integrated thermal swing adsorption (TSA) process for the removal of heavy hydrocarbons, acid gases, and water from a raw natural gas feed stream.

BRIEF DESCRIPTION OF THE DRAWINGS

FIG. 2 is intended as a non-limiting embodiment of the present invention.

DETAILED DESCRIPTION OF THE INVENTION

Figure 1:
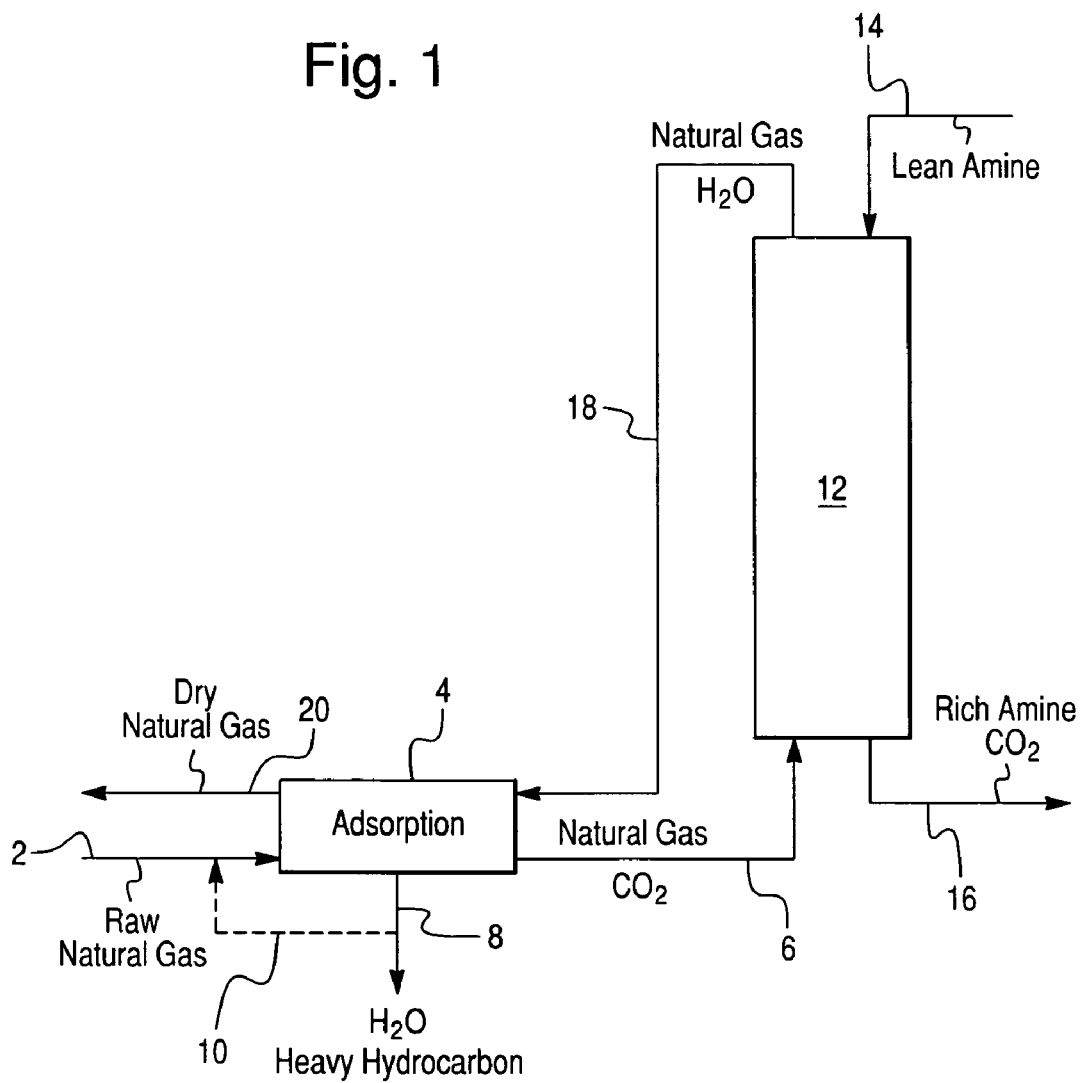
FIG. 1 is a schematic of an illustrative process for the removal of heavy hydrocarbons, $CO_2$, $H_2S$, and water from natural gas, and is intended as a non-limiting embodiment of the present invention.

The raw natural gas feed stream processed in accordance with the present invention can be any methane containing gas, which can also include heavy hderocarbons, water, carbon dioxide, hydrogen sulfide, and possibly other impurities such as mercaptans. The origin of the natural gas feed stream is not critical to this invention.

The present invention is directed to a novel process for the removal of carbon dioxides, hydrogen sulfides, and heavy hydrocarbons (e.g., $C_{4+}$ hydrocarbons, or more preferably $C_{6+}$ hydrocarbons) from a raw natural gas feed stream. More specifically, the present invention is directed to a multi-step process comprising a first step for the dehydration and removal of heavy hydrocarbons, a second step of aqueous amine treatment for the removal of acid gases, and a final step for the dehydration of the aqueous amine product effluent.

In general, the first step of the process involves the adsorptive removal of heavy hydrocarbons (e.g., $C_{4+}$ hydrocarbons, or more preferably $C_{6+}$ hydrocarbon, such as butane, pentane, hexane, and other heavier hydrocarbons) and water from a raw natural gas feed stream. One advantage of this step is that the heavier hydrocarbons can be recovered as a liquid product. A second advantage is that the downstream amine treatment is not subjected to high levels of heavy hydrocarbons, thereby reducing the potential for disadvantageous foaming. Optionally, the recovered heavy hydrocarbon stream can be added to the product gas stream thereby increasing the BTU value of the product gas. Another desirable feature of this invention comprises the regeneration of the hydrocarbon and water adsorbent, as discussed hereinbelow.

Any known heavy hydrocarbon and/or water adsorbent, employed as separate adsorbers in series or as a dual purpose adsorber can be used in this step, such as, silica gel, alumina, activated carbons, molecular sieves, or a combination thereof. The adsorbents used in the process of this invention may be employed in any useful physical form. This includes fine powders, shaped particles such as fluidizable microspheres, pellets, honeycombs, or in composites supported on substrates.

Useful molecular sieve adsorbents include, zeolite molecular sieves, EXS sieves, activated clays and the like. Molecular sieves include, for example, the various forms of silicoaluminophosphates, and aluminophosphates as disclosed in U.S. Pat. Nos. 4,440,871; 4,310,440; and 4,567,027, hereby incorporated by reference. Typical well-known zeolites which may be used include, chabazite, also referred to as Zeolite D, clinoptilolite, erionite, faujasite, also referred to as Zeolite X, and Zeolite Y, ferrierite, mordenite, Zeolite A and Zeolite P. Other zeolites that may be suitable for use according to the present invention are those having a high silica content, i.e., those having silica to alumina ratios greater than 10 and typically greater than 100, although such high zeolites are believed to have relatively low capacities for water. One such high silica zeolite is silicalite, as the term used herein includes both the silicapolymorph disclosed in U.S. Pat. No. 4,061,724 and also the F-silicalite disclosed in U.S. Pat. No. 4,073,865, hereby incorporated by reference.

EXS molecular sieves are distinguished from other molecular sieves by possessing octahedrally coordinated active sites in the crystalline structure. These molecular sieves contain electrostatically charged units that are radically different from charged units in conventional tetrahedrally coordinated molecular sieves such as in the classic zeolites. Members of the EXS family of sieves include, by way of example, ETS-4 (U.S. Pat. No. 4,938,939), ETS-10 (U.S. Pat. No. 4,853,202) and ETAS-10 (U.S. Pat. No. 5,244,650), all of which are titanium silicates or titanium aluminum silicates. The disclosures of each of the listed patents are incorporated herein by reference. The EXS sieves exhibit isotherms at temperatures slightly above ambient indicating the more active binding of organic species whereas at these temperatures, polar species show only minimal adsorption. As a consequence, organic species such as aliphatic and aromatic hydrocarbons can be selectively adsorbed from polar streams such as a natural feed gas stream containing polar species of $H_2S$, $CO_2$ and water.

It is particularly useful to employ one or more silica gel adsorbents, which selectively adsorbs $C_{4+}$ hydrocarbons and not the methane from the raw feed. An example of such an adsorbent is Sorbead®, e.g., Sorbead® R, Sorbead® H, and Sorbead® WS, or combinations thereof, available from Engelhard Corp, which has a preferential adsorption strength such that water is most strongly adsorbed, followed by heavier hydrocarbons, generally in the direction of decreasing molecular weight (thus, hexane is preferably adsorbed over pentane, which is preferably adsorbed over butane).

The second stage of the process involves an acid gas treatment plant for the removal of polar gases such as hydrogen sulfide and carbon dioxide. The acid gas removal is typically achieved with an aqueous lean amine stream, which absorbs essentially all of the hydrogen sulfide and carbon dioxide and other acid gases from the first adsorption effluent stream. In the amine treatment process the acid gas ($CO_2$ and $H_2S$) reacts to form weak chemical bonds with the amine solvent at high pressure, in which these chemical bonds permit the removal of the acid gas while the natural gas hydrocarbons pass through the solvent, and are available as a product reduced in these undesirable components. It is further understood that other acid gas solvents may be used and that the use of amine solutions as herein described and indicated in the drawings include other such acid gas solvents. These lean acid gas removal solutions can include alkanolamine solutions such as methyl diethanolamine, a physical solvent such as sulfolane, Selexol®, N-methylpyrolidone, a mixture of alkanolamine plus a physical solvent such as sulfinol solution, an inorganic solvent such as potassium carbonate, an organic solvent such as propylene carbonate, an organic solvent in combination with an alkanolamine or any other weak organic compounds such as piperazine, or hydroxy ethyl piperazine.

The amine solvents of the present invention are typically aqueous solutions, and thus, the natural gas product effluent from amine treatment is saturated with water. Therefore, the third step of the process involves the dehydration of the product effluent stream from aqueous amine treatment, to yield a dry natural gas product stream. This requires a dehydration process downstream from the amine treatment. In general, this dehydration step can be done with any known method for dehydration of a gas stream. In a preferred embodiment, the water can be adsorbed with an adsorbent selective for water, e.g. Sorbead®, previously used for hydrocarbon and water removal from the natural gas feed stream. Thus, a useful and efficient integrated process is used.

The three-step process of the present invention described above, i.e. heavy hydrocarbon and water adsorption, aqueous lean amine treatment, and subsequent dehydration by adsorption can be integrated as shown in FIG. 1. In FIG. 1, a raw natural gas stream 2, containing methane, carbon dioxide and hydrocarbons such as ethane, propane, butane, pentane, heavier hydrocarbons, and water is directed to an adsorption system 4, which contains a heavy hydrocarbon and water selective adsorbent. In an alternative embodiment, the adsorption system may contain one or more adsorbents selective for heavy hydrocarbons and water. At a predetermined point this first adsorption step comprising the adsorption of water and heavy hydrocarbons is terminated thereby producing a first adsorption effluent stream 6, which is a dehydrated and substantially heavy hydrocarbon free natural gas stream. Typically, the stream 6 is rich in methane. The first adsorption effluent stream 6 contains heavy hydrocarbon reduced natural gas along with acid gases such as $CO_2$ and $H_2S$, which can be removed by an amine treatment absorber 12. The first adsorption effluent stream 6 is passed into the bottom of an amine treatment absorber 12. An aqueous lean amine solution from line 14 flows down from the top of the amine treatment absorber 12 counter-current to the flow of the first adsorption effluent stream 6 and absorbs from the natural gas stream acid gases such as hydrogen sulfide, carbon dioxide. The removal of carbon dioxide and hydrogen sulfide produces a natural gas product effluent stream 18 from amine treatment free of these acid gases. A second waste stream 16 in the form of a rich amine solution (containing acid gases such as $CO_2$ and $H_2S$) leaves the amine treatment absorber 12 from the bottom of the absorber. Because the aqueous lean amine solvent used in the amine treatment absorber 12 is a mixture with liquid water, the natural gas product effluent 18 from amine treatment is saturated with water. To remove this water, the natural gas product effluent 18 from amine treatment is once again subjected to dehydration via the adsorption system 4, which contains a heavy hydrocarbon and water selective adsorbent, as previously described. This dehydration step results in a product natural gas stream 20, which is a dehydrated methane gas stream, free from acid gases, and heavy hydrocarbons. Optionally, the adsorbent of the adsorption system 4 can be desorbed and regenerated before this second water adsorption step, resulting in a first waste gas stream 8. The heavy hydrocarbon content of waste gas stream 8 represents lost heating value as well as lost chemical value if not recovered. Waste gas stream 8 can be cooled to condense the heavy hydrocarbons, and can optionally be re-circulated back to raw natural gas feed stream 2 via line 10 to recover any methane lost in waste gas stream 8.

Figure 3:
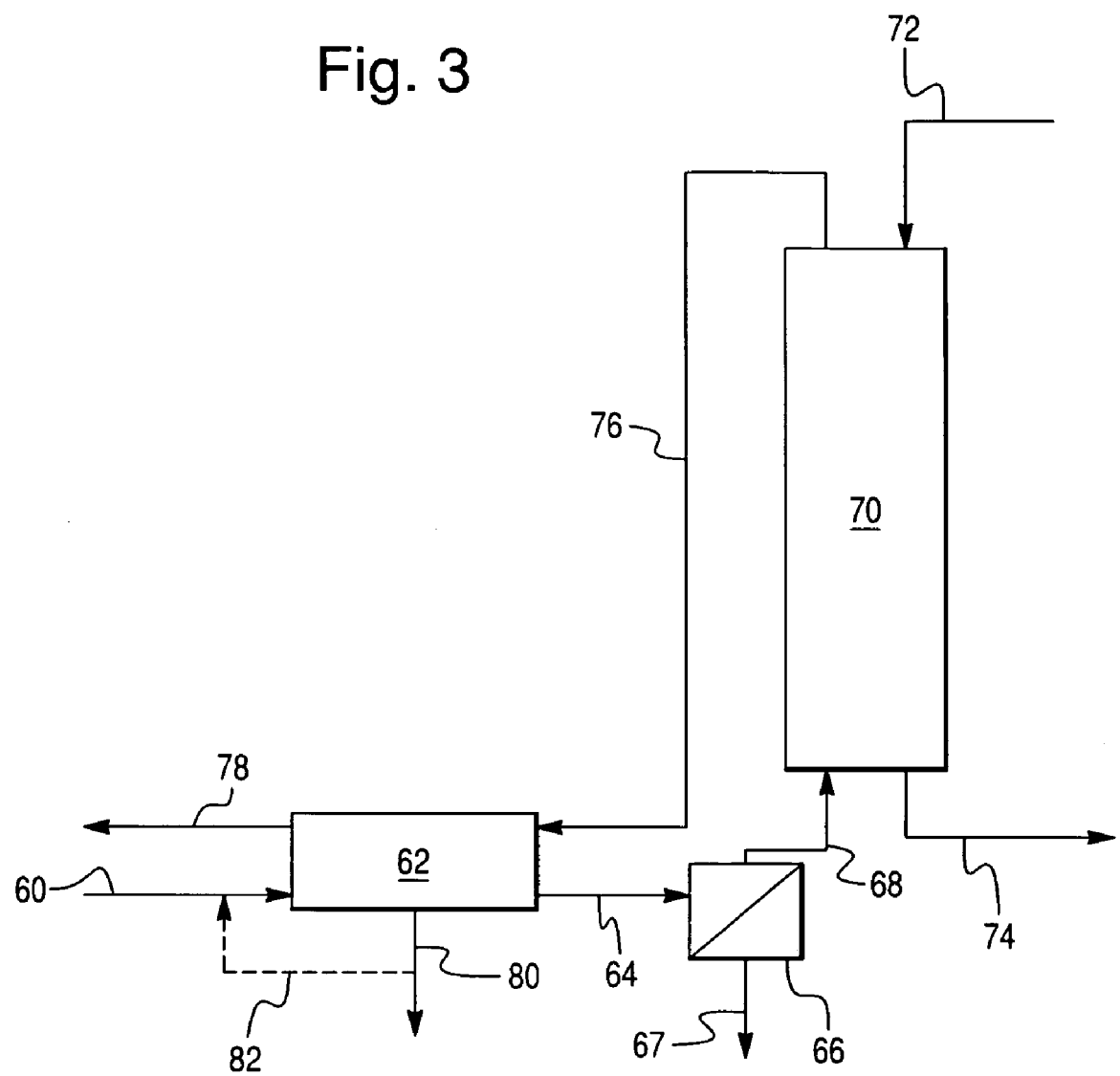
FIG. 3 is a schematic of an alternative embodiment illustrating a process for the removal of heavy hydrocarbons, $CO_2$, $H_2S$, and water from natural gas, and is intended as a non-limiting embodiment of the present invention.

FIG. 3 illustrates a process of this invention that can include a bulk acid gas removal membrane for the removal of acid gases prior to amine treatment. Such process may be useful if the $CO_2$ content of the natural gas stream is at least 10 volume %. As shown in FIG. 3, a raw natural gas stream 60, containing methane, carbon dioxide, heavier hydrocarbons, and water is directed to an adsorption system 62, which contains a heavy hydrocarbon and water selective adsorbent. At a predetermined point this first adsorption step comprising the adsorption of water and heavy hydrocarbons is terminated thereby producing a first adsorption effluent stream 64, which is a dehydrated and substantially heavy hydrocarbon-free natural gas stream. The first adsorption effluent stream 64 contains heavy hydrocarbon-reduced natural gas along with acid gases such as $CO_2$ and $H_2S$, which can be removed by an acid gas bulk removal membrane 66. Bulk removal membranes, which are well known in the art (see e.g., U.S. Pat. Nos. 4,130,403; 4,639,257 and 5,233,837), operate by selective permeation of $CO_2$ from high pressure to low pressure across a polymeric membrane. For example, the bulk removal membrane 66 can be selected from the group consisting of polysulfone, polyimid, polyamide, glassy polymer, and cellulose acetate. Removal of acid gases via membrane 66 results in a second effluent stream 68, which has a reduced acid gas content relative to stream 64 and an acid gas waste stream 67. The remaining steps of this process are similar to those previously shown in FIG. 1. Briefly, for substantially complete removal of remaining acid gases an amine treatment absorber 70 is used. In this step, second effluent stream 68 is passed through an amine treatment absorber 70. An aqueous lean amine solution from line 72 flows counter-current to the flow of the first adsorption effluent stream 68 and absorbs acid gases from the natural gas stream thereby producing a natural gas product effluent stream 76. A second waste stream 74 a rich amine solution (containing acid gases) leaves the amine treatment absorber 70. The natural gas product effluent 76 from amine treatment is saturated with water. To remove this water, the natural gas product effluent 76 is once again subjected to dehydration via the adsorption system 62, which contains a heavy hydrocarbon and water selective adsorbent, as previously described. This dehydration step results in a product natural gas stream 78, which is a dehydrated methane gas stream, essentially free from acid gases, and heavy hydrocarbons. The adsorbent of the adsorption system 62 can be desorbed and regenerated, resulting in a first waste gas stream 80. The heavy hydrocarbon content of waste gas stream 80 represents lost heating value as well as lost chemical value if not recovered. Accordingly, waste gas stream 80 can be cooled to condense and recover the heavy hydrocarbons, and then re-circulated to raw natural gas feed stream 60 via line 82 to recover any methane lost in waste gas stream 80.

The adsorption process of the present invention, used to remove water and hydrocarbons from the natural gas, can be accomplished by a thermal swing adsorption. Thermal swing adsorption processes are generally known in the art for various types of adsorptive separations. Generally, thermal swing processes utilize the process steps of adsorption at a low temperature, regeneration at an elevated temperature with a hot purge gas, and a subsequent cooling down to the adsorption temperature. One process for drying gases generally exemplary of thermal swing processes is described in U.S. Pat. No. 4,484,933, issued to Cohen. The patent describes basic thermal swing processing steps coupled with the use of an auxiliary adsorber bed for improving the regeneration step. Thermal swing processes are often used for drying gases and liquids and for purification where trace impurities are to be removed. Often thermal swing processes are employed when the components to be adsorbed are strongly adsorbed on the adsorbent, i.e., water, and thus, heat is required for regeneration.

Accordingly, the temperatures employed during the process of the present invention are essential to the invention, in particular for regeneration purposes. In a thermal swing process, the regeneration temperature must be higher than the adsorption temperature in order to effect the desorption of water and higher hydrocarbons. During the first adsorption step, which employs an adsorbent for the adsorption of water and heavy hydrocarbons from a raw natural gas feed stream, the temperature is preferably maintained at less than 150° F., and more preferably from about 60° to about 120° F. In the desorption step of the present invention, the heavy hydrocarbons and water adsorbed by the adsorbent in the first step are released from the adsorbent, thus regenerating the adsorbent, at temperatures preferably from about 300° to about 550° F.

In this regeneration step, part of one of the gas streams of the present invention, for instance the raw natural gas feed stream, the product effluent from the adsorption unit or a waste stream from a downstream process, can be heated and the heated stream circulated through the adsorbent to desorb the adsorbed components. It is particularly useful to employ a hot purge stream comprising a heated raw natural gas stream for regeneration of the adsorbent. Alternatively, the source can be from outside the processes of the present invention. Regeneration can be carried out in a direction cocurrent or counter-current to that of the adsorption step.

The pressures used during the adsorption and regeneration steps are generally elevated at typically 800 to 1200 psig. Typically, heavy hydrocarbon and water adsorption is carried out at pressures close to that of the feed stream and the regeneration steps may be conducted at about the adsorption pressure or at a reduced pressure. When a portion of an adsorption effluent stream is used as a purge gas, it is preferred in one aspect of the invention that the regeneration be conducted at about the adsorption pressure, especially when the waste or purge stream is re-introduced into the raw natural gas stream, for example. However, it is important to note that although the pressure reduction may assist in the regeneration of the adsorbent, the regeneration is primarily conducted thermally.

In the TSA process, the raw natural gas feed stream is passed to an adsorption system comprising three steps: (1) water and heavy hydrocarbons are removed by adsorption by an adsorbent selective for said heavy hydrocarbons and water; (2) acid gases are removed by an amine treatment with an aqueous lean amine solution; and (3) the product effluent stream from amine treatment is dehydrated by adsorption on an adsorbent selective for water. In a preferred embodiment the first (1) and second (3) adsorption steps occur in the same TSA unit. A particularly useful adsorbent for use in the TSA unit is one or more silica gels, preferably Sorbead® R, Sorbead® H, or Sorbead® WS, or combinations thereof.

More specifically, the process comprises four or more identical columns, each containing the same adsorbent. At any given time, two of these columns are involved in adsorption processes, one pre-amine treatment for the adsorption of heavy hydrocarbons and water and the other post-amine treatment for the adsorption of water from the amine treatment plant. Of the other two columns, one is undergoing the regeneration process, employing a heated purge gas stream to release previously adsorbed heavy hydrocarbons and water from the adsorbent, as previously described, and the other is being cooled process, typically employing a cool temperature gas stream to cool the column after the regeneration process. In one embodiment, the raw natural gas feed stream is used to cool the adsorbent column after thermal regeneration. The effluent stream from this cooling process can then be heated with an external heating source, e.g., a fired heater to 300-550° F., and redirected though another adsorbent column thereby causing the adsorbent therein to release trapped heavy hydrocarbons and water into the waste gas stream, thus, regenerating the adsorbent column for further adsorption cycles.

Accordingly, the first and second adsorption steps, desorption, and cooling steps of the present invention operate as multiple timed cycles of adsorption and desorption. The cycle times used in the first and second adsorption steps, desorption, and cooling steps of the process are not critical to the process except that longer times may require larger amounts of adsorbent. Typical cycle times range from 30 minutes to 4 hours.

Figure 2:
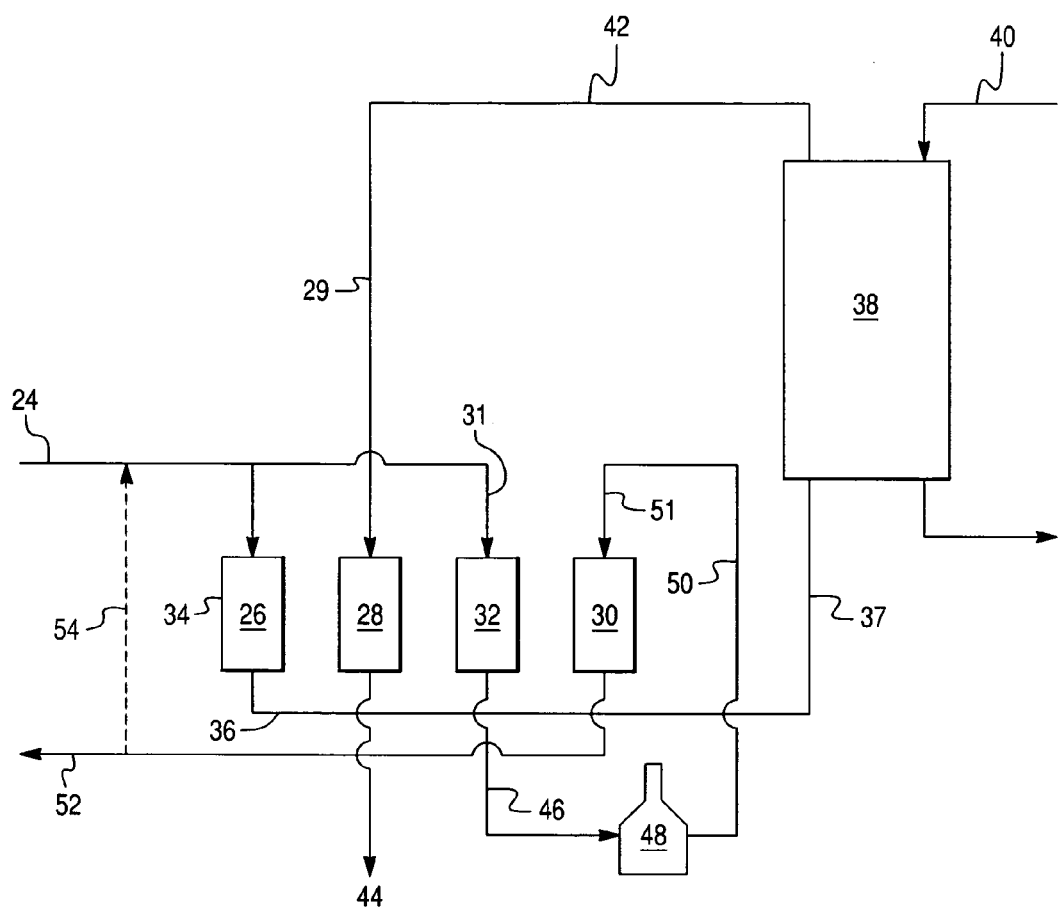
FIG. 2 is a more detailed schematic of an illustrative thermal swing adsorption (TSA) process for the removal of $C_{4+}$ hydrocarbons, $CO_2$, $H_2S$, and water from natural gas, and shows the regeneration of the adsorbent used therein.

More specific process parameters are now given with respect to the operation of the integrated TSA process of the present invention, for the removal of heavy hydrocarbons, water, carbon dioxide, and hydrogen sulfide from a raw natural gas stream, by reference to FIG. 2. In FIG. 2, the TSA system 34 illustrated comprises four columns 26, 28, 30, and 32. During a four hour total process cycle, each of the TSA columns will alternately rotate through the processes steps of: (1) a first adsorption step, for the pre-amine treatment removal of heavy hydrocarbons and water; (2) a second adsorption, for the post-amine treatment removal of water; (3) heat regeneration with a heated stream; and (4) cooling with a low temperature gas stream. Thus, at any give time in a continuous purification process two of the columns will be involved in adsorption processes, represented by columns 26 and 28, and the remaining two undergoing regeneration and cooling processes, represented by columns 30 and 32, respectively.

Referring to FIG. 2 a raw natural gas stream 24, containing methane, carbon dioxide and hydrocarbons such as ethane, propane, butane, and heavier hydrocarbons, is directed to a TSA adsorption system 34, comprising four separate and identical columns each containing an identical adsorbent selective for heavy hydrocarbons and water. In one embodiment the heavy hydrocarbon and water adsorbent is a silica gel, e.g., Sorbead® R, Sorbead® H, or Sorbead® WS. In an alternative embodiment, one or more silica gels can be used, e.g., a combination of one or more of Sorbead® R, Sorbead® H, and Sorbead® WS. The adsorption of water and heavy hydrocarbons by the adsorbent in column 26 from the raw natural gas feed stream 24 produces a first adsorption effluent stream 36, which is a dehydrated, substantially heavy hydrocarbon free methane stream. In addition to enriched methane gas, the first adsorption effluent stream 36 also contains acid gases such as $CO_2$ and $H_2S$, which can be subsequently removed by an amine treatment absorber 38. The removal of heavy hydrocarbons prior to amine treatment is preferred not only because the heavy hydrocarbons can be recovered as an economic benefit, but further such hydrocarbon can cause foaming problems during amine treatment, thereby reducing the amine gas capacity for the reduction of carbon dioxide. The first adsorption effluent stream 36 is passed via line 37 into the bottom of an amine treatment absorber 38. An aqueous lean amine solvent 40 flows down from the top of the absorber 38 counter-current to the flow of the first adsorption effluent stream 36 and absorbs from the natural gas stream acid gases such as hydrogen sulfide, and carbon dioxide. The amine treatment results in a natural gas product effluent 42 from amine treatment absorber 38 substantially free of acid gases such as $CO_2$ and $H_2S$. Because the amine solvent used in the amine treatment absorber 38 is a mixture with liquid water, the natural gas product effluent 42 from amine treatment is saturated with water. To remove this water, the natural gas product effluent 42 from amine treatment is directed to dehydration in column 28 via line 29, which column comprises a heavy hydrocarbon and water selective adsorbent, as previously described. The natural gas product effluent 42 from amine treatment is passed through adsorbent column 28 wherein water and heavy hydrocarbons are adsorbed from the second adsorbent effluent stream 42, thereby resulting in a product natural gas stream 44, which comprises a dehydrated natural gas substantially free of heavy hydrocarbons and acid gases. The second adsorption step of water removal downstream of the amine treatment may displace some quantity of heavy hydrocarbons and direct this incremental amount of heavy hydrocarbons into the product natural gas stream 44, however, the product natural gas stream 44 is still substantially free of heavy hydrocarbons.

Columns 30 and 32 are representative of the regeneration and cooling processes, which occur during the TSA process in each of the adsorbent columns. Thermal regeneration is described by referring to column 30 and is accomplished by heating raw natural gas feed stream 24 to a temperature of at least 300° F. using, for example, a fired heater 48 and passing resultant heated gas stream 50 via line 51 through column 30. The regeneration of adsorbent column 30 results in a waste or purge gas stream 52 comprising heavy hydrocarbons and water. The waste or purge gas stream can be cooled allowing for a portion of the water and heavy hydrocarbons to be condensed as a liquid stream, which can be removed from the process. Optionally, the waste or purge gas stream 52 can be re-circulated back to the raw natural gas feed stream 24 via line 54. Cooling is preferentially done using the raw natural gas feed stream 24 prior to any heating of said stream. The cooling process is represented by column 32. Thus, for example, natural gas stream 24 can be passed through column 32 via line 31 thereby cooling column 32 prior to use as an adsorbent for the adsorption of heavy hydrocarbons and water. Once each column is regenerated and cooled, the column can be recirculated to the starting point of the TSA system, as represented by column 26, thus, allowing for the integrated purification process to be continuous. Optionally, the effluent stream from the cooling column 32 can be passed through the heater 48 via line 46 and the heated gas stream 50 used for thermal regeneration, as previously described.

In an alternative embodiment, in cases where the raw natural gas feed steam has a low heavy hydrocarbon content, the first adsorption step, can be skipped and the raw natural gas feed stream can be sent directly to the amine treatment step. The process of this embodiment would be carried out as previously described, starting with amine treatment.

What is claimed is:

1. A process for the purification of a raw natural gas feed stream, wherein said process comprising the steps of:

(1) passing said raw natural gas feed stream through an adsorbent unit containing an adsorbent, said adsorbent selective for removal of heavy hydrocarbons and water from said natural gas feed stream, and thereby forming a first effluent stream;

(2) passing said first effluent stream in contact with an aqueous amine absorbent, wherein said aqueous amine absorbent removes acid gases from said first effluent stream thereby forming a natural gas product effluent having an acid gas content less than said first effluent stream;

(3) recirculating said natural gas product effluent through said adsorbent unit containing an adsorbent selective for removal of water;

(4) collecting a natural gas product stream having an amount of water and heavy hydrocarbons less than said raw natural gas stream; and (5) wherein said adsorbent in said adsorbent unit is regenerated by the release of the adsorbed heavy hydrocarbons and water using a heated purge stream.

2. The process of claim 1, wherein said adsorbent selective for removal of heavy hydrocarbons and water is selected from the group consisting of silica gels, molecular sieves, activated aluminas, activated carbons, and a combination thereof.

3. The process of claim 2, wherein said adsorbent is one or more silica gels.

4. The process of claim 1, wherein said adsorbent in said adsorbent unit is regenerated using a heated raw natural gas feed stream, wherein said regeneration results in a waste stream comprising heavy hydrocarbons.

5. The process of claim 4, wherein said waste stream is re-circulated to said raw natural gas product stream.

6. The process of claim 4, wherein said waste gas stream is cooled to partially condense the water and heavy hydrocarbons resulting in a vapor stream substantially reduced in water and heavy hydrocarbons.

7. The process of claim 6 wherein said vapor stream is re-circulated to said raw natural gas feed stream.

8. The process of claim 6, wherein said vapor stream is re-circulated to said first effluent stream.

9. The process of claim 1, wherein a bulk aid gas membrane used for the bulk removal of acid gases is placed between said adsorbent and said aqueous amine absorbent.

10. A natural gas purification system to dehydrate and remove heavy hydrocarbons from a raw natural gas stream comprising:

(1) a first adsorption unit comprising a first adsorbent, wherein said first adsorbent is selective for the adsorption of heavy hydrocarbons and water;

(2) an amine treatment absorber for the absorption of acid gases to produce an acid gas-reduced effluent having an acid gas content less than said raw natural gas stream;

(3) means to direct effluent from said first adsorption unit to said amine treatment absorber;

(4) means to direct said acid gas-reduced effluent to said first adsorption unit comprising second adsorbent selective for removal of water; and (5) a heating means for regeneration of said first and said second adsorbents, wherein said hearing means comprises means to heat raw natural gas feed stream and means to direct said heated raw natural gas stream through said first and second adsorbents, said regeneration resulting in a waste stream comprising heavy hydrocarbons and water.

11. A natural gas purification system of claim 10, wherein said first adsorbent or said second adsorbent is selected from the group consisting of silica gels, molecular sieves, activated aluminas, activated carbons, and a combination thereof.

12. The natural gas purification system of claim 10, wherein said first adsorbent and said second adsorbent comprise the same adsorbent.

13. The natural gas purification system of claim 12, wherein said adsorbent is one or more silica gels.

14. The natural gas purification system of claim 10, wherein said system provides a means for re-circulating said waste stream to said raw natural gas feed.

15. The natural gas purification system of claim 10, wherein said system provides a means for cooling and condensing water and heavy hydrocarbons from said waste stream resulting in a vapor stream substantially devoid of water and heavy hydrocarbons and re-circulating said vapor stream to said raw natural gas stream.

16. The natural gas purification system of claim 10, wherein a bulk acid gas membrane used for the bulk removal of acid gases is placed between said adsorbent unit and said aqueous amine adsorbent.

17. A natural gas purification system of claim 10, wherein said adsorption unit comprises at least four columns, each of said columns containing an adsorbent selective for the adsorption of water and heavy hydrocarbons, wherein said adsorbent is selected from the group consisting of silica gels, molecular sieves, activated aluminas, activated carbons, and a combination thereof.

18. The natural gas purification system of claim 17, wherein said columns are identical columns each containing the same adsorbent, which is selective for the adsorption of heavy hydrocarbons and water.

19. The process claim 1, wherein said adsorption unit comprises four columns, each of said columns containing an adsorbent selective for the adsorption of water and heavy hydrocarbons.

20. The process of claim 19, wherein said adsorption unit operates as a multiple timed cycle wherein each of said first, second, third, and fourth columns cycle through each of four sequential steps, comprising of:

(1) the pre-amine treatment adsorption of heavy hydrocarbons and water;

(2) the post-amine treatment adsorption of water;

(3) the heat regeneration using a heated gas stream; and (4) the cooling using a non-heated gas stream; and wherein each column is simultaneously in a different one of said sequential steps.

* * * * *